(12) United States Patent
Seretse et al.

(10) Patent No.: US 12,303,653 B2
(45) Date of Patent: May 20, 2025

(54) ELONGATE MEDICAL TOOLS INCLUDING PRINTED CIRCUIT BOARDS

(71) Applicant: Pacesetter, Inc., Sylmar, CA (US)

(72) Inventors: Amanuel Seretse, New Brighton, MN (US); Jason M. Romanowski, Bloomington, MN (US); Andy Blommer, Plymouth, MN (US); Patrick P. Senarith, Maple Grove, MN (US)

(73) Assignee: Pacesetter, Inc., Sylmar (CA)

( * ) Notice: Subject to any disclaimer, the term of this patent is extended or adjusted under 35 U.S.C. 154(b) by 808 days.

(21) Appl. No.: 17/517,859

(22) Filed: Nov. 3, 2021

(65) Prior Publication Data

US 2022/0054799 A1   Feb. 24, 2022

Related U.S. Application Data

(62) Division of application No. 16/379,605, filed on Apr. 9, 2019, now Pat. No. 11,191,923.

(51) Int. Cl.
*A61B 5/00* (2006.01)
*A61M 25/00* (2006.01)
*H05K 1/02* (2006.01)
*H05K 1/11* (2006.01)
*H05K 1/18* (2006.01)
*H05K 3/00* (2006.01)

(52) U.S. Cl.
CPC ....... *A61M 25/0097* (2013.01); *A61B 5/6852* (2013.01); *H05K 1/0277* (2013.01); *H05K 1/11* (2013.01); *H05K 1/181* (2013.01); *H05K 3/0014* (2013.01); *A61M 2207/00* (2013.01); *H05K 2201/10151* (2013.01)

(58) Field of Classification Search
CPC ......... A61B 2562/12; A61B 2562/125; A61M 25/0097; A61M 2207/00
See application file for complete search history.

(56) References Cited

U.S. PATENT DOCUMENTS 5,465,717 A * 11/1995 Imran .................... A61N 1/056
                                                            600/374
2017/0224237 A1* 8/2017 Basu .................. A61B 18/1492

* cited by examiner

*Primary Examiner* — Livius R. Cazan
(74) *Attorney, Agent, or Firm* — Dean D. Small; The Small Patent Law Group, LLC

(57) ABSTRACT

A tool adapted for insertion into a physiological lumen of a patient is provided. The tool includes a hub, a core extending distally from the hub, and a printed circuit board (PCB) assembly. The PCB assembly includes a PCB substrate coupled to the core and an electronic component disposed on the PCB substrate and electrically coupled to the hub. The tool further includes an outer sheath disposed about each of the core and the PCB assembly an outer sheath disposed about each of the core and the PCB assembly. The PCB substrate may be in the form of a ring disposed at a distal end or about the core or may be a flexible PCB substrate adapted to be wrapped about the core and coupled to the core using an adhesive backing.

20 Claims, 14 Drawing Sheets

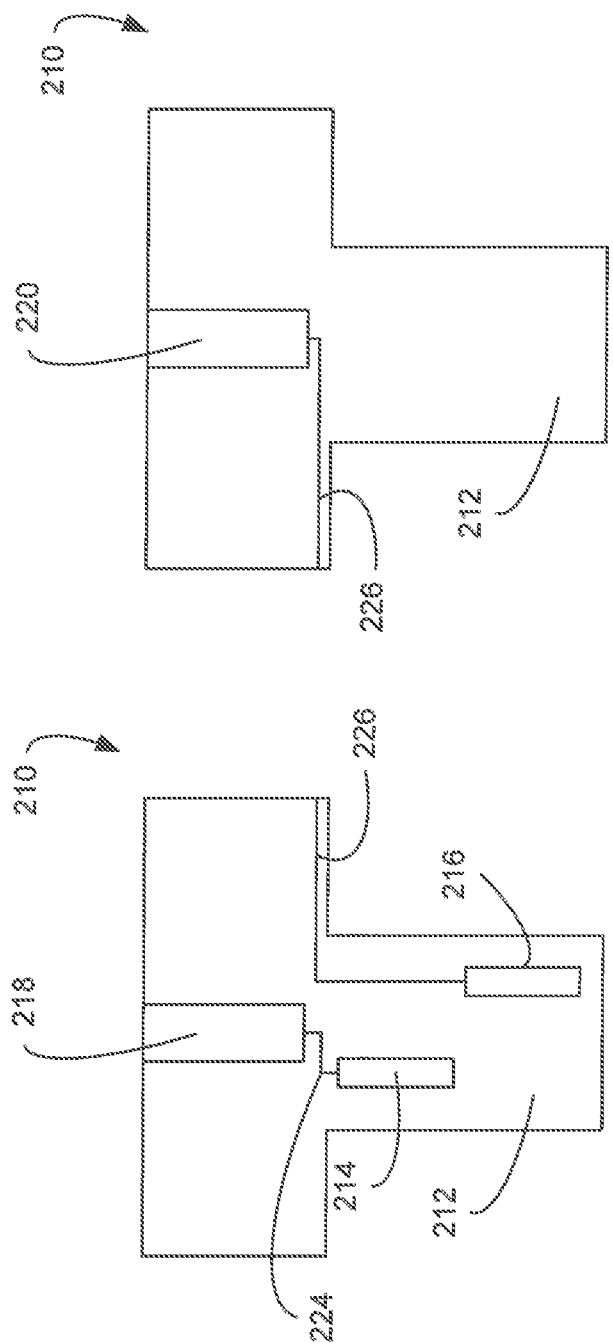

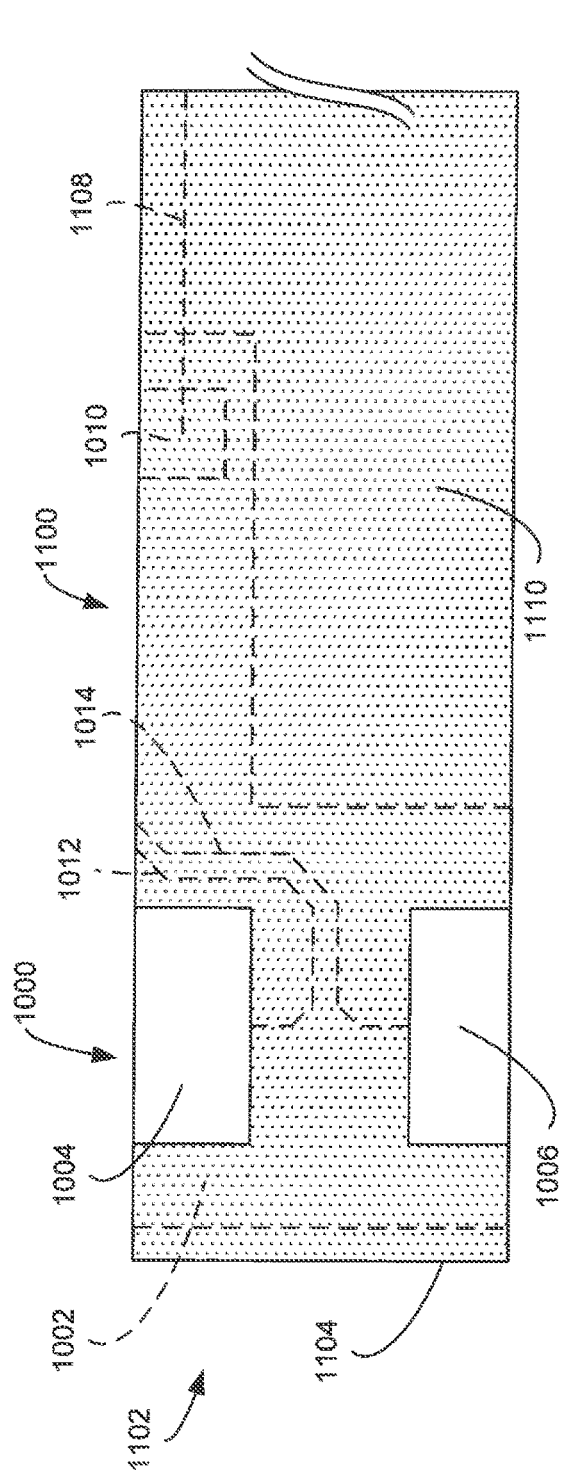
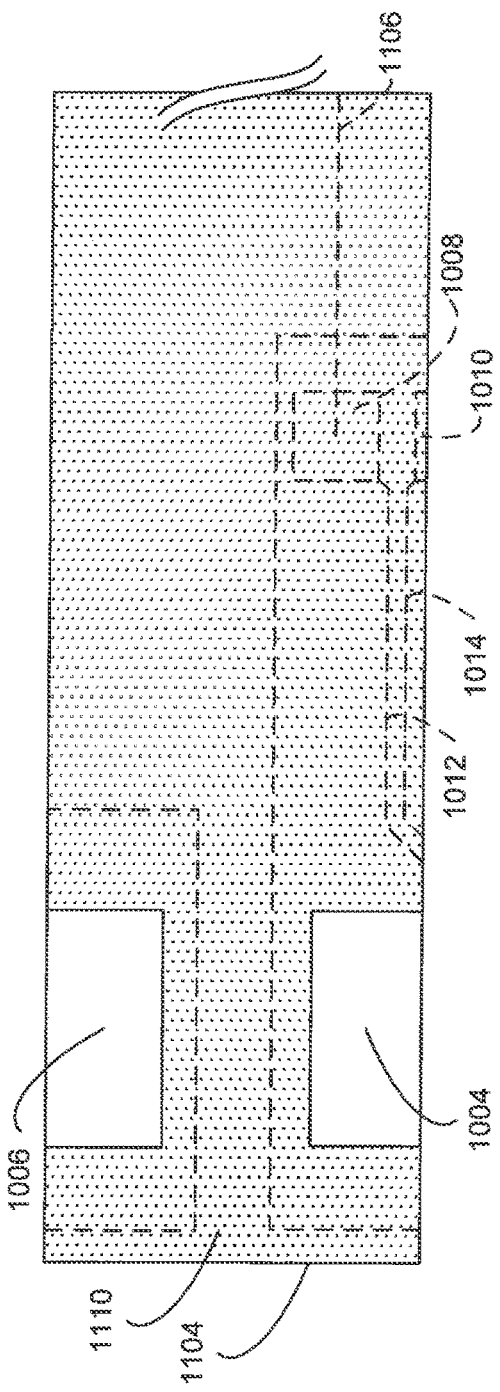
FIG. 11A
FIG. 11B

ELONGATE MEDICAL TOOLS INCLUDING PRINTED CIRCUIT BOARDS

CROSS REFERENCE TO RELATED APPLICATION

The present application is a divisional application of U.S. application Ser. No. 16/379,605 filed Apr. 9, 2019, which application is hereby incorporated by reference in its entirety.

FIELD OF THE INVENTION

Aspects of the present disclosure relate to catheters and, more specifically, to catheters including sensors and leads for conducting various medical procedures.

BACKGROUND

Various diagnostic and therapeutic procedures in or on the body of a patient, such as in the circulatory system, heart chambers, the bronchial tree or the like, may be performed or facilitated by inserting a catheter or similar elongate medical tool, such as a catheter or guide wire into a physiological lumen and thereafter navigating the diagnostic or therapeutic tool to the target anatomical site.

One method for maneuvering a catheter/guide wire involves the use of fluoroscopy to track the position of a catheter/guide wire, during navigation or ablation. Another method of maneuvering a catheter and guide wire to an operational site is to place one or more position sensors/leads on the catheter and guide wire, track the sensors with a navigation system, and display a real-time or rendered image of the catheter/guide wire for the clinician manipulating the catheter/guide wire to view.

In many medical procedures, various physiological and location data within the body of a patient need to be monitored and analyzed. The raw signal generated by the sensor located within the body is transmitted to an external device, in which the signal is re-translated into physiological data, which may be subsequently processed, displayed (e.g., on a monitor), and/or saved or otherwise stored. In addition to or instead of sensors for collecting and processing location-related data, catheters may further include electrodes, sensors, or other electrical components for performing various other tasks including, without limitation, ablation, pacing and/or sensing of cardiac tissue, measurement of electrical activity within tissue, and the like.

It is with the foregoing in mind that the following concepts were conceived and developed.

SUMMARY OF THE DISCLOSURE

In one aspect of the present disclosure, a tool adapted for insertion into a physiological lumen of a patient is provided. The tool includes a hub, a core extending distally from the hub, and a printed circuit board (PCB) assembly. The PCB assembly includes a PCB substrate coupled to the core and an electronic component disposed on the PCB substrate and electrically coupled to the hub. The tool further includes an outer sheath disposed about each of the core and the PCB assembly an outer sheath disposed about each of the core and the PCB assembly.

In one implementation, the PCB substrate is flexible and wrapped about a portion of the core. In such implementations, the PCB substrate may include an adhesive backing and may be coupled to the core by the adhesive backing. The PCB assembly may further include a terminal point and a trace extending along the PCB substrate to electrically couple the terminal point to the electronic component, the terminal point being further electrically coupled to the hub such that the electronic component is electrically coupled to the hub. In such implementations, the PCB substrate may extend distally from a proximal end of the core and the terminal point may be disposed at the proximal end of the core such that the electronic component is disposed distal the terminal point.

In another implementation, the electronic component is an electrode. In such implementations, the electrode may be disposed at a distal end of the core. The electrode may also be exposed through the outer sheath.

In yet another implementation, the PCB substrate has a ring shape. In such implementations, the PCB substrate may be coupled to a distal end of the core. The ring shape may be any of a complete ring, a split ring, and a multi-part ring. In certain implementations, the ring-shaped PCB substrate is coupled to the distal end of the core by a sheath disposed about each of the core and the PCB assembly.

In still another implementation the tool is one of a guidewire and a catheter.

In yet another implementation, the electronic component is one of an electrode and a sensor.

In another aspect of the present disclosure, a method of assembling a tool adapted for insertion into a physiological lumen of a patient is provided. The method includes obtaining a core having an elongate shape and disposing a printed circuit board (PCB) assembly onto the core, the PCB assembly including a PCB substrate and an electronic component disposed on the PCB substrate. The method further includes coupling the PCB substrate to the core, electrically coupling the electronic component to a hub coupled to the core, and applying an outer sheath about the core and the PCB assembly.

In one implementation, the PCB substrate includes an adhesive backing and coupling the PCB substrate to the core comprises bonding the PCB substrate to the core using the adhesive backing.

In another implementation, applying the outer sheath about the core and the PCB assembly couples the PCB substrate to the core.

In yet another implementation, the method further comprises, after applying the outer sheath, removing a portion of the outer sheath to expose the electronic component.

In still another implementation, the core is a tubular core and the tool is a catheter.

In yet another aspect of the present disclosure a catheter assembly is provided. The catheter assembly includes a hub, a tubular core extending distally from the hub, and a PCB assembly. The PCB assembly includes a PCB substrate coupled to the tubular core by an adhesive backing of the PCB substrate. The PCB assembly further includes a first electrode disposed on the PCB substrate and electrically coupled to a first terminal point of the PCB assembly and a second electrode disposed on the PCB substrate and electrically coupled to a second terminal point of the PCB assembly. The catheter assembly further includes an outer sheath disposed about each of the tubular core and the PCB assembly. Each of the first terminal point and the second terminal point are electrically coupled to the hub and each of the first electrode and the second electrode are exposed through the outer sheath.

BRIEF DESCRIPTION OF THE DRAWINGS

FIGS. 4A and 4B are schematic illustrations of a ring assembly for use in the catheters of FIGS. 2 and 3.

FIGS. 11A and 11B are side views of a distal end of a tool including the PCB assembly of FIG. 10.

DETAILED DESCRIPTION

Figure 1:
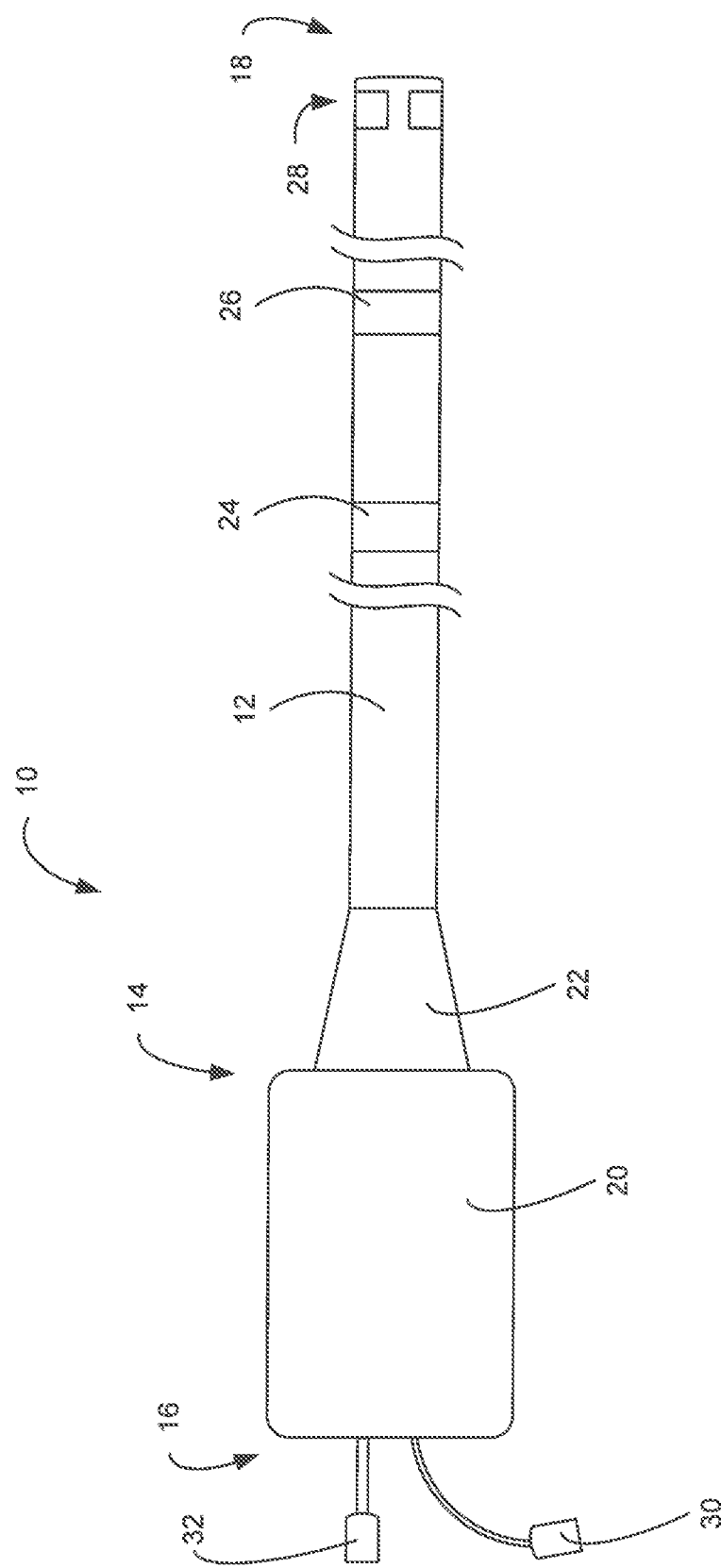
FIG. 1 is a side view of a catheter 10 in accordance with an implementation of the present invention.

Implementations of the present disclosure involve medical tools including printed circuit board (PCB) elements. Although not limited to any particular type of tool, such tools may include catheters, guide wires, and other elongate tools for insertion into physiological lumens of a patient and which include electronic components (e.g., electrodes, sensors, etc.) for performing various functions as described below. As further described below, by incorporating the various electronic components into a PCB, significant improvements in manufacturing efficiency and quality may be achieved.

As previously noted, catheters, guide wires, and other similar tools may include various electronic components for performing such data collection and analysis. As previously noted, such components may be used to locate the tool, obtain measurements from within a physiological lumen, and/or stimulate tissue adjacent the tool. Regardless of the function of such components, each generally requires the exchange of electrical current/signals between the component and a proximal end of the tool. In certain implementations, such signals may be relatively low energy and correspond to sensor measurements or similar signals exchanged between components of the tool. Alternatively or in addition to such signals, the electrical components may also be adapted to connect to and deliver power from a power source for purposes of stimulating or ablating tissue or performing similar tasks.

In light of the foregoing, a given tool may include sensors and/or electrodes for obtaining measurements or delivering energy to adjacent tissue, but also includes cables, wires, leads, etc. for transmitting electrical signals to/from the sensor or electrode. Such conductors are generally routed along the tool such that during use, they extend out from the physiological lumen within which the tool is disposed an external computing device. The conductors are generally extended along or are otherwise supported by an inner structure (generally referred to herein as a "core" or a "tubular core" in the context of catheter-based applications) which may include a metal wire, a braided wire, a plastic tube, or combinations thereof (e.g., a plastic tube including an embedded braided wire). In addition to supporting the various components of the tool, the core may provide structural integrity to the tool and enable manipulation of the tool (e.g., by being coupled to pull rings of the tool).

Electrical current typically enters or exits the tool at an electrical connection attached to the proximal end of the tool and, as a result, generally requires that multiple sections of the tool be electrically isolated from each other and the surrounding tissue. For example, such isolated areas need to be protected from ingress of bodily fluid that may result in a short or other conductivity issues.

In one specific example, a catheter may include a pair of electrodes disposed at its distal end for measuring electrical activity in adjacent tissue and/or stimulating the tissue. The use of such electrodes may present various manufacturability concerns due to the variation present when the electrode is adhered to the underlying polymer of the catheter. Also, conventional approaches to manufacturing such catheters can be complicated and time consuming. For example, the distal assembly may require the folding of the electrodes and soldering of associated wires while maintaining a certain gap between the electrodes. Moreover, many conventional assembly processes are manual and tedious, directly impacting the ultimate cost and effectiveness of the catheter.

Various aspects of the present disclosure are directed to simplifying the manufacturing process of elongate tools including electronic components and, as a result, to improving manufacturing efficiency and improving quality by reducing part-to-part variation. More specifically, aspects of the present disclosure are directed to catheters and similar elongate tools that include PCBs. In at least certain implementations, such PCB assemblies are in the form of a ring that may be coupled to a distal end of a core of a catheter (or similar tool) or otherwise disposed at various locations along the catheter. The ring assembly may be coupled to the core using various techniques; however, in one implementation, a polymer sleeve is disposed about each of the ring assembly and the core and heat-shrunk/reflowed to couple the ring assembly to the core. In addition to coupling the ring assembly and core, the polymer sleeve adds rigidity and electrical insulation to the distal end of the catheter.

In another implementation of the present disclosure, the PCB is in the form of a flexible PCB that may extend along a portion of the core. In one implementation, the flexible PCB is adapted to be coupled to a distal end of the core while in other implementations the flexible PCB extends along a greater length of the core, including substantially along the full length of the core. Although the flexible PCB may be coupled to the core using various methods, in at least one implementation, the flexible PCB is adhesive-backed such that, during assembly, the flexible PCB may be laid or otherwise run along the length of the core and held in place by the adhesive. Subsequently, an outer sheath may be heat-shrunk/reflowed over the flexible PCB.

FIG. 1 is a side view of a catheter 10 in accordance with an implementation of the present invention. The catheter 10 may be used in any medical procedure requiring catheterization and that includes is not intended to be limited to any particular type of catheter or catheterization procedure. The catheter 10 includes a catheter shaft 12 and a hub 14. The catheter shaft 12 has a proximal portion 16 and a distal portion 18. In some embodiments, the catheter shaft 12 may, for example, be any catheter shaft, whether known now or later developed, for use in the delivery and/or deployment of implantable medical devices (such as medical electrical leads, stents and implantable sensors) or other catheterization procedures (such as drug delivery, mapping and ablation).

The catheter shaft 12 may be formed of a single layer or two or more distinct layers that are formed of the same or different materials. In some implementations, the catheter shaft 12 may include reinforcing materials such as metallic or polymeric braids. The catheter shaft 12 may be formed of one or more thermoplastic polymers such as, but not limited to polytetrafluoroethylene (PTFE), ethylene tetrafluoroethylene (ETFE), fluorinated ethylene propylene (FEP), polyoxymethylene (POM, for example, DELRIN™ available from DuPont), polyether block ester, polyurethane, polypropylene (PP), polyvinylchloride (PVC), polyether-ester (for example, ARNITEL™ available from DSM Engineering Plastics), ether or ester based copolymers (for example, butylene/poly(alkylene ether) phthalate and/or polyester elastomers such as HYTREL™ available from DuPont), polyamide (for example, DURETHAN™ available from Bayer or CRISTAMID™ available from Elf Atochem), elastomeric polyamides, block polyamide/ethers, polyether block amide (PEBA, for example, available under the trade name PEBAX™, silicones, polyethylene (PE), Marlex high-density polyethylene, Marlex low-density polyethylene, linear low density polyethylene (for example REXELL™ polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR™), polysulfone, nylon, nylon-12 (such as GRILAMID™ available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof.

In some implementations, the catheter shaft 12 or at least an outer layer thereof may be formed of a polyether block amide such as PEBAX™. A variety of PEBAX™ materials are available, having varying performance parameters such as hardness/stiffness as indicated by the durometer value of a particular PEBAX™ polymer. In one particular implementation, the catheter shaft 12 or an outer layer thereof may be formed of PEBAX™ having a Shore hardness of about 72 D.

In some implementations, as illustrated, the hub 14 may include a body portion 20 and a strain relief portion 22. The body portion 20 may include a lumen (not shown) in communication with one or more lumens (not shown) extending through the catheter shaft 12. The body portion 20 may also include one or more luer fittings to accommodate attachment of fluid lines and the like. The body portion 20 may be configured to act as a handle or grip and thus may include structure (not illustrated) that facilitates grasping the hub 14. The hub 14 may be a breakaway or splittable hub.

In some implementations, the strain relief portion 22 may be integrally molded with the body portion 20. The strain relief portion 22 may include an inner component that is integrally molded or otherwise formed with the body portion 20 and one or more external components that help provide desired characteristics such as a flexibility/stiffness gradient between the catheter shaft 12 and the hub 14.

The hub 14 may be formed of a variety of different materials. Suitable materials include but are not limited to the materials discussed above with respect to the catheter shaft 12. In some cases, the hub 14 may be formed of a material that does not bond well, either adhesively or via welding, to the material used to form the catheter shaft 12.

In some embodiments, the hub 14 may be formed of a thermoset polymer. In some embodiments, at least part of the hub 14, such as the body portion 20 and an inner component of the strain relief portion 22 may be formed of a styrene-butadiene copolymer available commercially under the K-Resin™ name. The catheter shaft 12, or at least an outer layer thereof, may be formed of a material that is difficult to secure to the hub 14 using an adhesive or by directly welding the two together. In some cases, the addition of a mechanical connection between the catheter shaft 12 and the hub 14 may be beneficial.

As illustrated in FIG. 1, the catheter 10 may include various electrical components adapted to perform various functions. The electrical components may include, for example and without limitation, various sensors and electrodes disposed at different locations along the catheter shaft 12 to provide location data, measure physiological activity, provide stimulation, ablate tissue, or perform or facilitate any other of a wide range of functions and activities. The catheter 10 of FIG. 1, for example, includes each of a pair of ring electrodes 24, 26 disposed at an intermediate location along the catheter shaft 12 between the proximal portion 16 and the distal portion 18. In one non-limiting example, each of the ring electrodes 24, 26 may at least one of deliver electrical stimulation to adjacent tissue or measure electrical activity of such tissue. The catheter 10 may also include a distal tip assembly 28 that further includes additional sensors and/or electrodes for performing any of the foregoing functions.

To facilitate functions of the various electrical components of the catheter 10, the hub 20 may include one or more connectors, such as connectors 30 and 32. Each connector 30, 32 may be electrically coupled to a respective sensor, electrode, or other component of the catheter 10 via a cable, wire, lead, or similar conductor or conductors (not shown). In general, the connectors 30, 32 may be communicatively coupled to other devices configured to transmit electrical signals to the electrical components of the catheter 10 and/or receive electrical signals from the electrical components of the catheter 10. Such devices may include, for example and without limitation, power sources, computing devices, data recorders, displays, and the like. Each connector 30, 32 may be electrically coupled to one, two, or any number of electrical components of the catheter 10. For example, in one implementation, each of the ring electrodes 24, 26 may be electrically coupled to the connector 30, which in turn may be electrically coupleable to a computing device capable or recording and/or storing data corresponding to signals from the ring electrodes 24, 26.

Tools Including PCB Assembly Tips

With the foregoing general description of the catheter 10 in mind, one aspect of the present disclosure is directed to improved distal tip assemblies and methods of manufacturing catheters including such distal tip assemblies. As described below in further detail, the distal dip assemblies described herein are generally formed as an integrated printed circuit board (PCB) assembly that is connected to wires, leads, or similar conductors of the catheter. The PCB assembly is then coupled to the distal end of the catheter.

Figure 2:
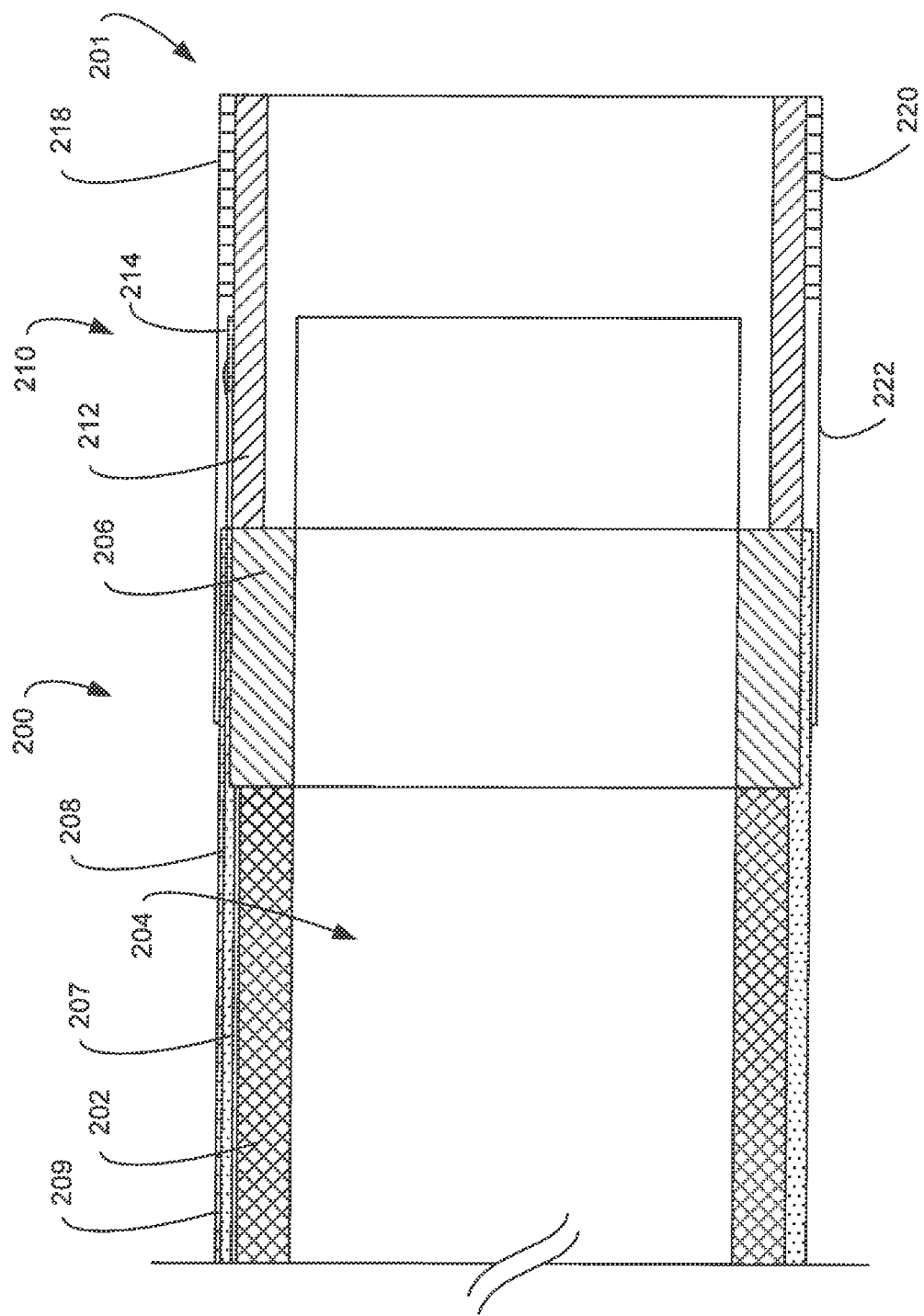
FIG. 2 is a cross-sectional side view of a distal end of another example catheter in accordance with the present disclosure.

FIG. 2 is a cross-sectional view of an example catheter 200 in accordance with the present disclosure and, more specifically, illustrates a distal end 201 of the catheter 200. The present disclosure is generally applicable to any catheter (or similar elongate tool, such as a guide wire); accordingly, the catheter 200 and its components are provided merely as an example and should not be viewed as limiting the scope of this disclosure.

As illustrated in FIG. 2, the catheter 200 generally includes a tubular core 202 defining a primary lumen 204. The lumen 204 may vary in size and shape according to the particular application for the catheter 200; however, in general, the lumen 204 is sized and shaped to facilitate insertion and translation of other tools therein.

In certain implementations, the catheter 200 may include a pull ring 206 from which a pull wire 207 proximally extends. During use, tension on the pull wire 207 may be varied to selectively deflect and/or straighten the catheter 200 to facilitate steering or other manipulation of the distal end of the catheter 200.

The catheter 200 may also include one or more conductors, such as conductor 208, extending along its length. The conductor 208 generally facilitates transmission of electrical signals along the length of the catheter 200. In the implementation illustrated in FIG. 2, the conductor 208 is illustrated as a single wire; however, it should be appreciated that the conductor(s) extending along the length of the catheter 200 may be in any suitable configuration including, without limitation, single wires and multi-wire cables. As shown, the tubular core 202 and the pull ring 206 may be encapsulated by an outer layer or sheath 209.

As illustrated in FIG. 2, each of the pull wire 207 and the conductor 208 are shown as being embedded within the tubular core 202; however, it should be appreciated that any suitable arrangement of pull wires and conductors may be used in implementations of the present disclosure. For example and without limitation, in certain implementations each of the pull wire 207 and the conductor 208 may be disposed on an external surface of the tubular core 202 and coupled to the tubular core 202, such as by applying/wrapping a sheath or similar layer about the core 202, the pull wire 207 and the conductor 208. In other implementations, the conductor 208 and the pull wire 207 may be integrated into the tubular core 202. In still other implementations, the tubular core 202 may be formed from multiple layers and the pull wire 207 and the conductor 208 may be disposed between adjacent layers of the tubular core 202. It should also be appreciated that either or both of the pull wire 207 and the conductor 208 may be disposed within a lumen defined by the tubular core 202 or within lumens embedded within the tubular core 202 and either or both of the pull wire 207 and the conductor 208 may be disposed in the same or respective lumens.

Figure 7A:
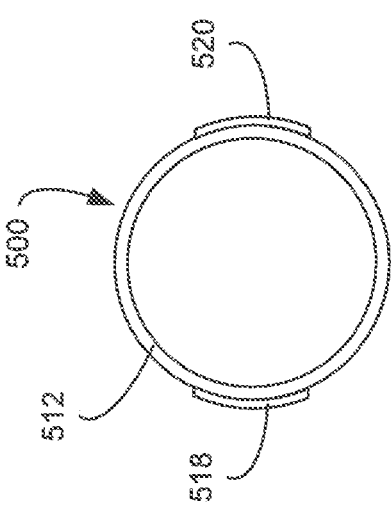
FIGS. 7A and 7B are end and side views of yet another ring assembly including a multi-part PCB substrate.
Figure 7B:
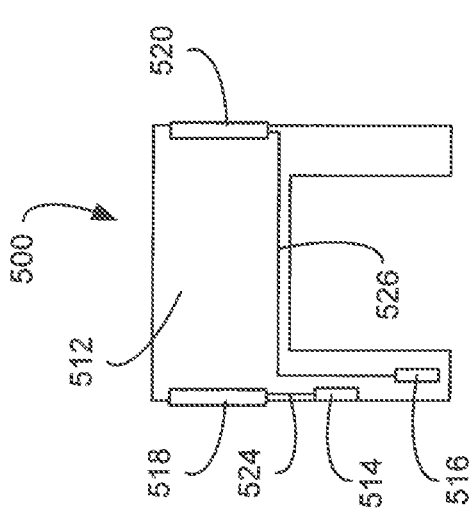

In implementations of the present disclosure, a PCB assembly 210 (also referred to herein as a ring assembly 210) is disposed at a distal end of the catheter 200. The ring assembly 210 generally includes a printed circuit board (PCB) substrate 212 on or within which various electrical components are integrated. To prevent obstruction of the lumen 204, the PCB substrate 212 has an annular or similar tubular shape. For example, in certain implementations (such as illustrated in FIGS. 5A-6B), the PCB substrate may be in the form of a rigid or semi-rigid ring or split ring. As illustrated in FIGS. 7A-7B, the PCB substrate 212 may also be divided into multiple discrete segments.

The PCB substrate 212 supports electrical components of the ring assembly 210 and may further include traces, contacts, and/or conductors for electrically connecting such components of the distal assembly 210 to each other and/or to other components of the catheter 200. For example, the ring assembly 210 illustrated in FIG. 2 includes a contact 214 to which the conductor 208 is electrically coupled. The ring assembly 210 further includes a pair of electrodes 218, 220 in electrical communication with the contact 214 such that electrical signals/electrical energy may be sent to or received from the electrodes 218, 220.

Although the ring assembly 210 may be coupled to the core 202 in various ways, in the specific implementation illustrated in FIG. 2, the core 202 and ring assembly 210 are joined by a coupling sleeve 222. As described below in further detail in the context of FIGS. 8A-8F, coupling using such an approach may include disposing the coupling sleeve 222 to extend along each of the core 202 (including any outer sheath extending around the core, such as the sheath 210, and/or pull ring that may be present, such as the pull ring 206) and the PCB substrate 212 of the ring assembly 210. Once so positioned, the coupling sleeve 222 may be heat shrunk/reflowed, thereby forming a joint between the tubular core 202 and PCB substrate 212.

Figure 3:
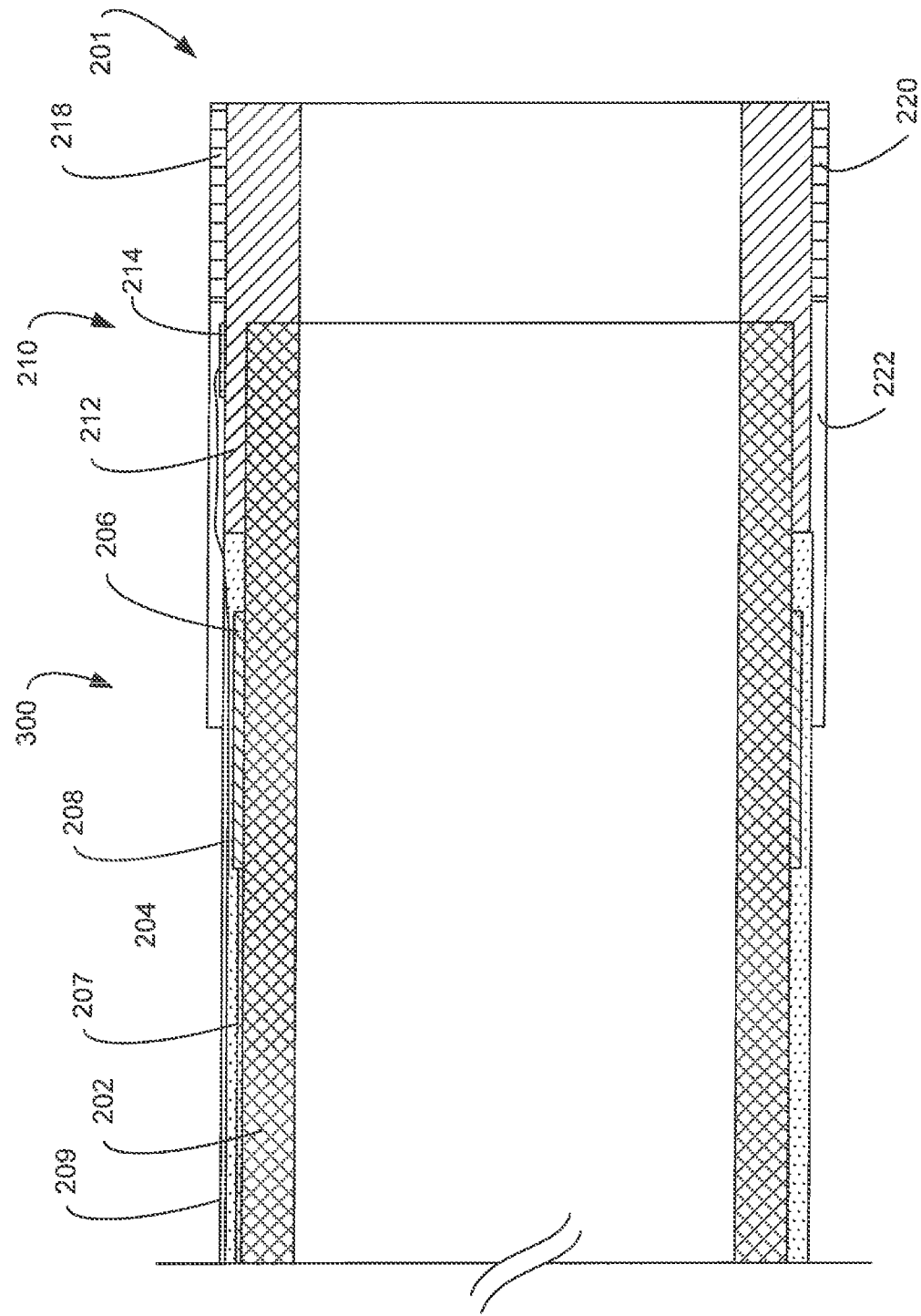
FIG. 3 is a cross-sectional side view of a distal end of yet another example catheter in accordance with the present disclosure.

In other implementations, the ring assembly 210 may be disposed onto a distal end of the core 202. For example, FIG. 3 illustrates an alternative implementation of a catheter 300 in which the core 202 extends beyond the pull ring 206 and the PCB substrate 212 of the ring assembly 210 is sized to "cap" or otherwise be disposed on the distal end of the core 202. In such implementations, the PCB substrate 212 may be coupled to the core 202 using any suitable method. Similar to the implementation of FIG. 2, for example, the implementation of FIG. 3 also includes a coupling sleeve 222 extending around and joining the PCB substrate 212 to the core 202 (or, more specifically, the sheath 212 extending about the core 202). In other implementations, adhesives, ultrasonic welding, or any other suitable method of coupling components may be used to join the PCB substrate 212 and core 202.

FIGS. 4A and 4B are elevation views of the PCB/ring assembly 210 of FIGS. 2 and 3. As previously discussed, the ring assembly 210 generally includes a PCB substrate 212 on which various electrical components are disposed. The ring assembly 210 further includes a pair of connector contacts 214, 216 coupled to respective electrodes 218, 220 by traces 224, 226. In certain implementations, the electrodes 218, 220 may be platinum electrodes; however, any suitable electrode material may be used.

It should be appreciated that the two-electrode ring assembly 210 illustrated in FIGS. 2-4B is provided merely as an example and other variations are contemplated as part of this disclosure. More generally, PCB assemblies in accordance with the present disclosure include electronic components (e.g., sensors, electrodes) disposed on a PCB substrate that is coupleable to a core of an elongate medical tool, such as a catheter or guide wire. The term "core" is used herein to generally describe an underlying structure of the medical tool and may include tubular structures, solid structures, or any combination thereof. In addition to the electronic components, the PCB assembly may include terminal points (e.g., contact pads) electrically connected to the electronic components (e.g., by directly coupling of the terminal point to the electronic component or by coupling the terminal point to the electronic component by a trace or similar conductor). PCB assemblies in accordance with the present disclosure are not limited to any particular number of electronic components or any particular arrangements of such components. Accordingly, to the extent any specific implementations are discussed herein, such implementations should be considered merely as illustrative examples of aspects of this disclosure.

Figure 5A:
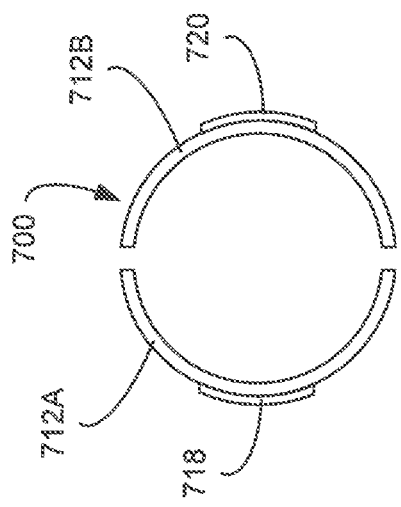
FIGS. 5A and 5B are end and side views, respectively, of a ring assembly including a printed circuit board (PCB) substrate in the shape of a complete ring.
Figure 5B:
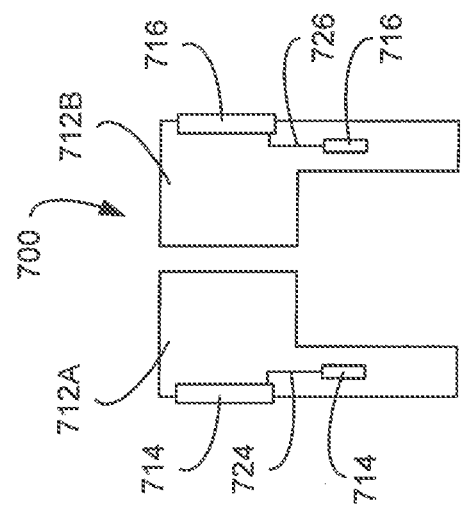
Figure 6A:
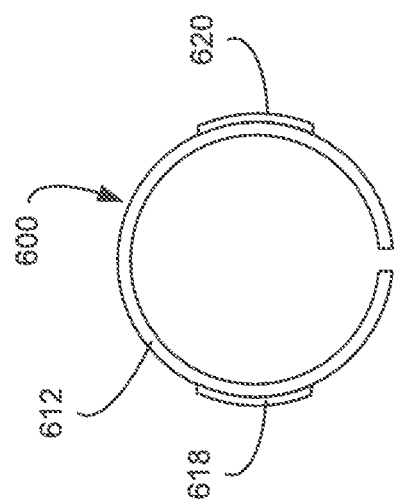
FIGS. 6A and 6B are end and side views of another ring assembly including a PCB substrate in the shape of a split ring.
Figure 6B:
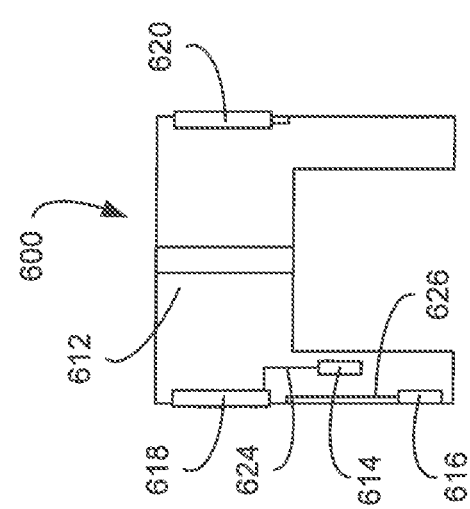

FIGS. 5A-7B illustrate different configurations of ring assemblies in accordance with the present disclosure. FIGS. 5A and 5B illustrate a ring assembly 500 consistent with that illustrated in FIGS. 4A and 4B. The ring assembly 500 includes a PCB substrate 512 in the form of a unitary ring. The ring assembly 500 further includes a pair of contacts 514, 516 connected to respective electrodes 518, 520 by traces 524, 526. FIGS. 6A and 6B illustrate an alternative ring assembly 600 including a PCB substrate 612. Similar to the ring assembly 500 of FIGS. 5A-5B, the ring assembly 600 further includes a pair of contacts 614, 616 connected to respective electrodes 618, 620 by traces 624, 626. In contrast, however, the PCB substrate 612 includes a split 601 such that the ring assembly 600 may be "snapped" onto a catheter core or otherwise permitted to expand to accommodate variations in catheter diameter. FIGS. 7A and 7B illustrate another alternative ring assembly 700 in which the PCB substrate is divided into two distinct halves 712A, 712B. Each half includes a respective contact 714, 716 with each contact 714, 716 connected to an electrode 718, 720 by traces 724, 726. Although illustrated as including two halves, it should be appreciated that in other implementations, any number of suitable PCB substrate parts may be used.

Although the foregoing description generally refers to the ring-type PCB assemblies being disposed at a distal end of the catheter, it should be appreciated that such assemblies may be located at any location along the length of the catheter. Moreover, while the ring assemblies are discussed as being used in conjunction with catheters, such ring assemblies may more generally be incorporated into any elongate body or tool. For example and without limitation, a ring assembly may be coupled to and used in conjunction with a guide wire.

Manufacturing of Elongate Tools with PCB Assemblies

Elongate tools, such as catheters, including PCB assemblies in accordance with the present disclosure may be manufactured in various ways; however, in general, the process of manufacturing such tools includes forming a primary tool body or shaft and disposing wiring along the tool body. The wiring is then electrically coupled to contacts of the PCB assembly, which, in turn, is disposed on a core of the tool. With the wiring connected and the PCB assembly in place, the PCB assembly is coupled to the core using one of various techniques.

FIG. 8A-8F illustrate an example assembly process for manufacturing an example catheter 800 in accordance with the present disclosure. Additional reference is made to FIG. 9, which is a flow chart describing a method 900 in accordance with the assembly steps illustrated in FIGS. 8A-8F.

Figure 8A:
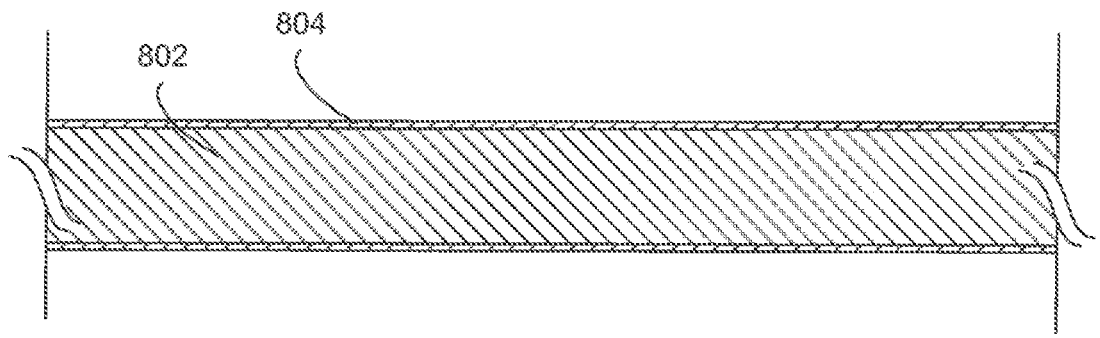
FIGS. 8A-8F are cross-sectional side views of a catheter at various stages of assembly of the catheter.
Figure 9:
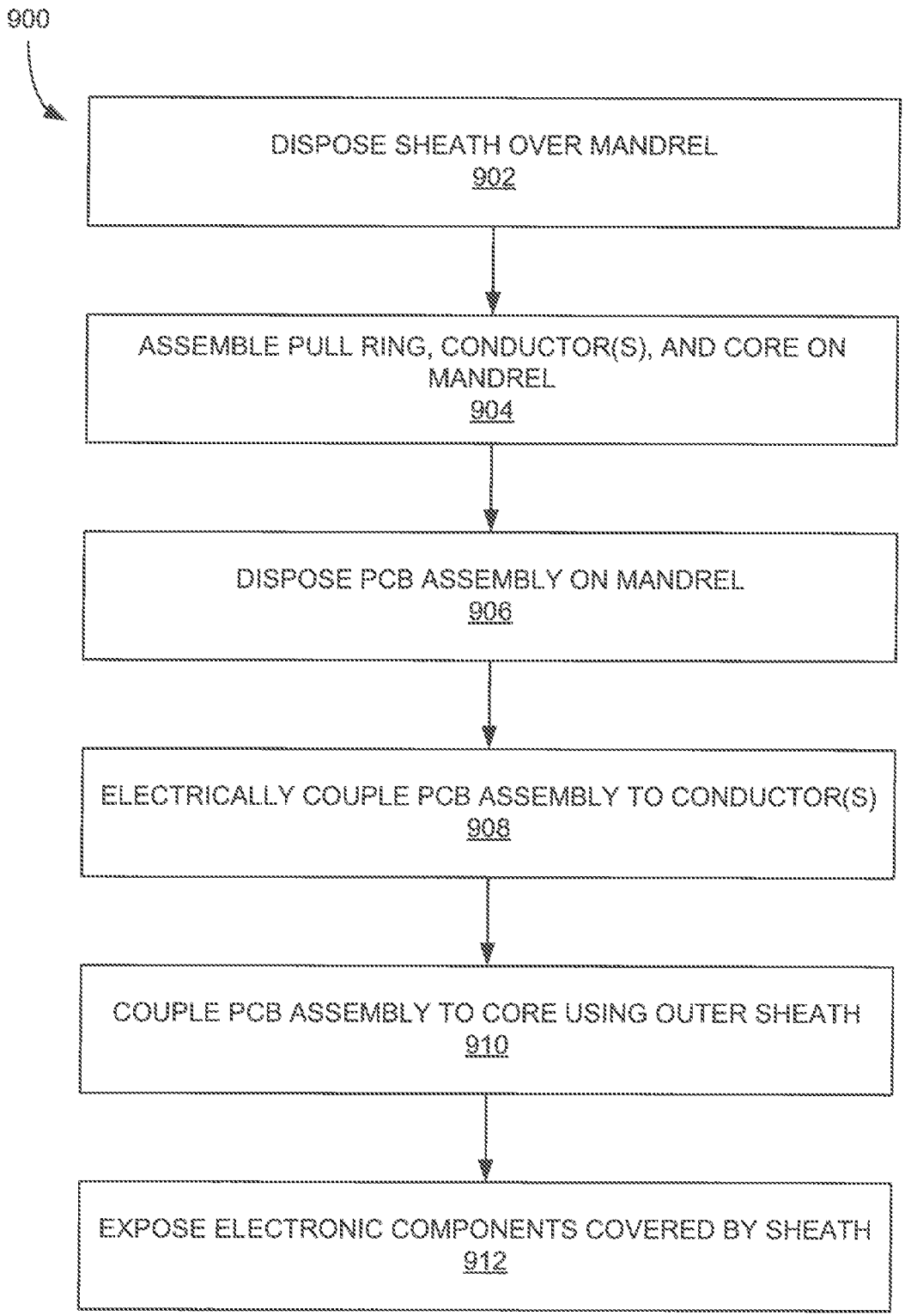
FIG. 9 is a flow chart illustrating a method for assembling a catheter in accordance with FIGS. 8A-8F.

Referring first to FIG. 8A and operation 902 of FIG. 9, a mandrel 802 for assembling the catheter is prepared. Preparation of the mandrel 802 may include, for example, disposing a sheath 804 about the mandrel. The sheath 804 may generally be used to reduce friction between the mandrel 802 and subsequent components slid onto the mandrel 802 during assembly of the catheter. In one example implementation, the sheath 804 may be formed from polytetrafluoroethylene (PTFE), or a similar low-friction material.

Figure 8B:
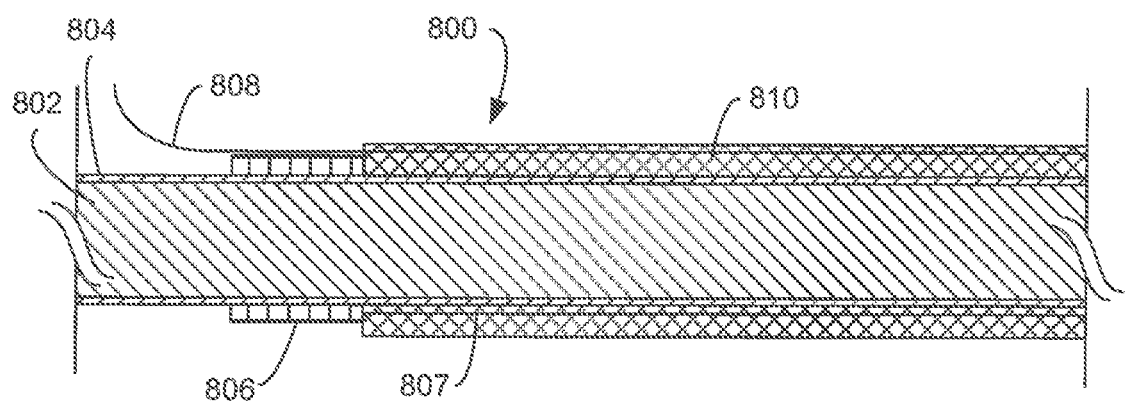

As illustrated in FIG. 8B, with the mandrel 802 prepared with the sheath 804, each of a pull ring 806, a conductor 808, and a tubular core 810 may be assembled onto the mandrel 802 (operation 904). The process of assembling the pull ring 806, conductor 808, and tubular core 810 may vary in implementations of the present disclosure; however, in general, the process includes extending the tubular core 810 along the mandrel 802, disposing the pull ring 806 on the mandrel 802, and running each of the conductor 808 and a pull wire 807 along the length of the tubular core 810. It should be appreciated that extending the tubular core 810 along the mandrel 802 may include disposing a pre-fabricated (e.g., an extruded) core along the mandrel, fabricating the core directly onto the mandrel (e.g., by braiding thread onto the mandrel and subsequently applying a layer of heat shrink), or any combination thereof. In certain implementations, the tubular core has a multi-layer construction and the pull wire 807 and the conductor 808 may be disposed between adjacent layers of the core 802. The pull wire 807 and the conductor 808 may also be disposed in a common or respective lumens that are in turn coupled to the exterior of the tubular core 810 (e.g., by applying a layer of shrink wrap) or that are embedded within the tubular core 810.

Figure 8C:
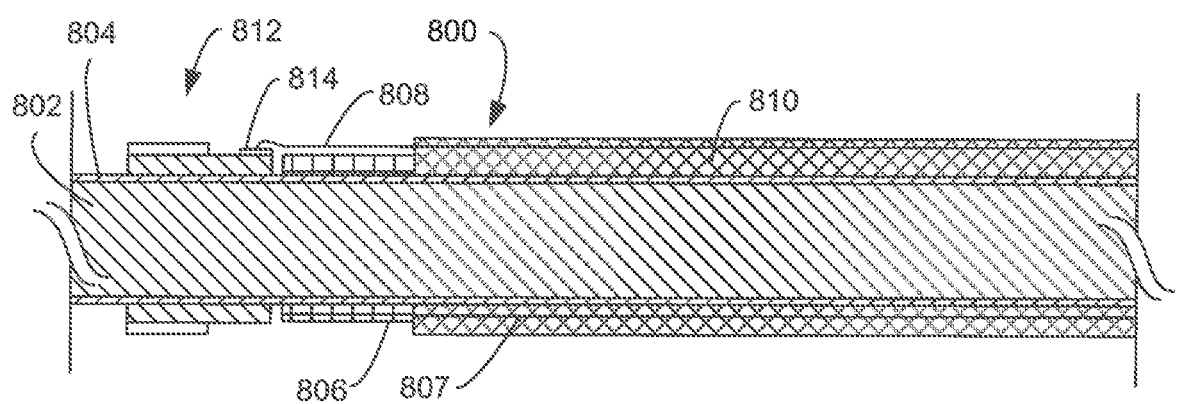

As illustrated in FIG. 8C, a PCB assembly 812 is subsequently disposed on the mandrel 802 distal the pull ring 806 and tubular core 810 (operation 906) and the conductor 808 is electrically coupled to a contact 814 of the PCB assembly 812 (operation 908). Disposing the PCB assembly 812 over the mandrel 802 may include any of sliding the PCB assembly 812 onto a distal end of the mandrel 802, "snapping" the PCB assembly 812 onto the mandrel 802 (e.g., when using a split ring assembly, similar to that of FIGS. 6A-6B), or disposing multiple portions of the PCB assembly 812 about the mandrel 802 (e.g., when using a multi-part ring assembly, similar to that of FIGS. 7A-7B). As previously noted in the context of FIG. 3, the PCB assembly 812 may also be adapted to at least partially extend over the tubular core 810 and/or the pull ring 806.

Figure 8D:
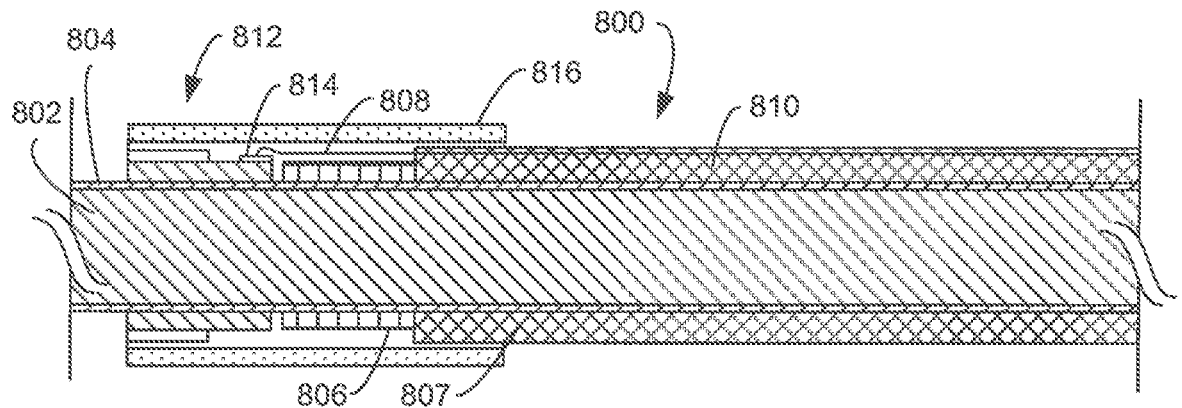
Figure 8E:
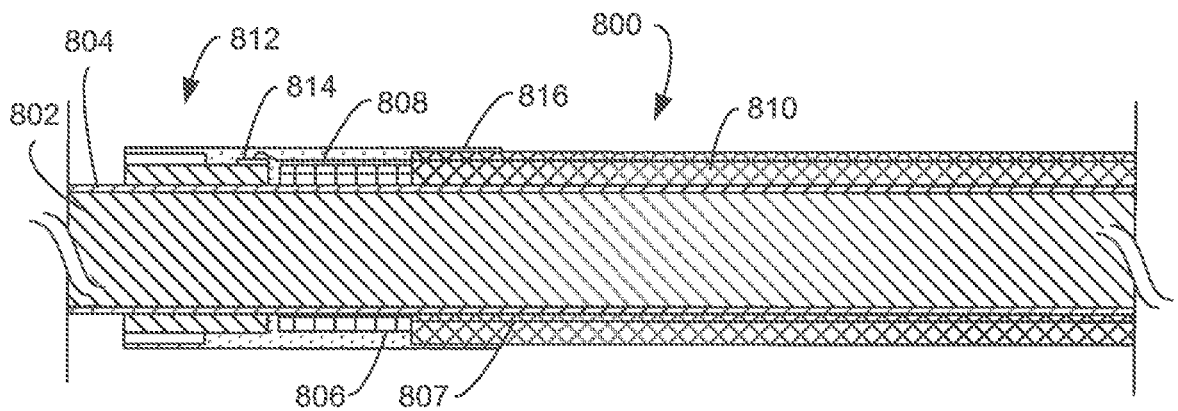
Figure 8F:
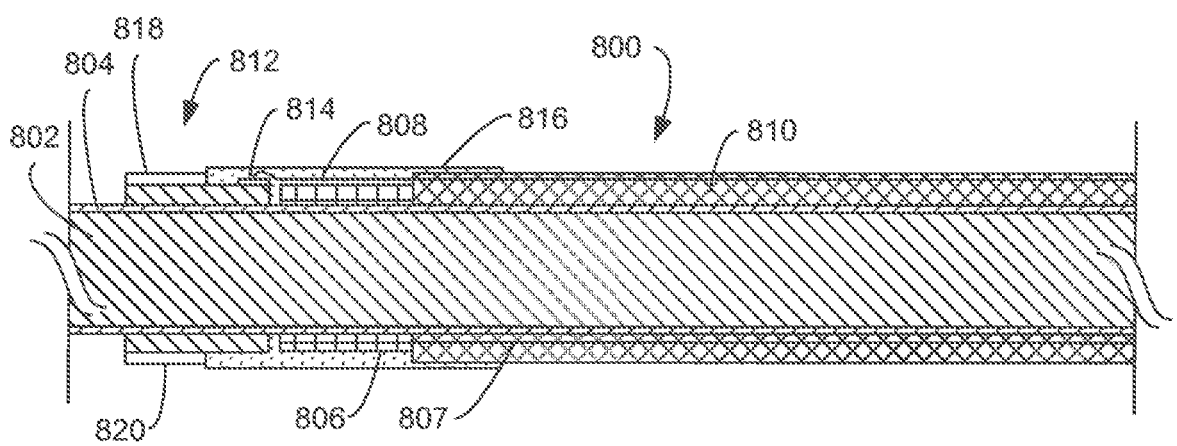

With the PCB assembly 812 in place and electrically coupled to the conductor 808, the PCB assembly 812 may then be coupled to the tubular core 810 (operation 910). In one implementation, such coupling may be achieved by using a sleeve 816 formed from a heat-shrinkable material. As shown in FIG. 8D, for example, the sleeve 816 may be disposed about a distal end of the catheter 800 such that the sleeve 816 extends about a portion of each of the PCB assembly 812 and the tubular core 810. As illustrated in FIG. 8E, a heating process may then be conducted to reflow/shrink the sleeve 816 about the tubular core 810 and the ring assembly 814, thereby coupling the tubular core 810 to the PCB assembly 812. Although the sleeve 816 is illustrated as extending over only a distal portion of the core 810 and PCB assembly 812, it should be appreciated that the sleeve 816 may extend further over a proximal portion of the core 810 up to and including the full length of the core 810.

As shown in FIG. 8E, following reflow of the distal sleeve 816, the distal sleeve 816 may at least partially obstruct electrodes 818, 820 (or similar components) of the PCB assembly 812. Accordingly, following coupling of the PCB assembly 812 to the tubular core 810, portions of the sleeve 816 may be removed to increase exposure of the electrodes 818, 820 (operation 912). For example and without limitation, removing portions of the sleeve 816 may include one of cutting away or ablating (e.g., using a laser) portions of the sleeve 816. The catheter 800 including the PCB assembly 812 may subsequently be removed from the mandrel 802.

As previously noted, each of the sleeve 816 and layers of the core 810 may be formed from a material capable of being heat shrunk/reflowed. Although various materials may be used in applications of the present disclosure, in at least certain implementations and without limitations, such a material may include a polyether block amide (e.g., PEBAX™).

Medical Tools Including Flexible PCB Assemblies

The PCB assemblies of the various foregoing examples were illustrated as including a PCB substrate having a substantially static shape and, more specifically, a curved or circular shape conforming to the overall shape of the catheter. However, it should be appreciated that in other aspects of the present disclosure, the PCB assembly may be a more general assembly formed from a flexible circuit that is wrapped around or otherwise coupled to a tubular core of the catheter.

Figure 10:
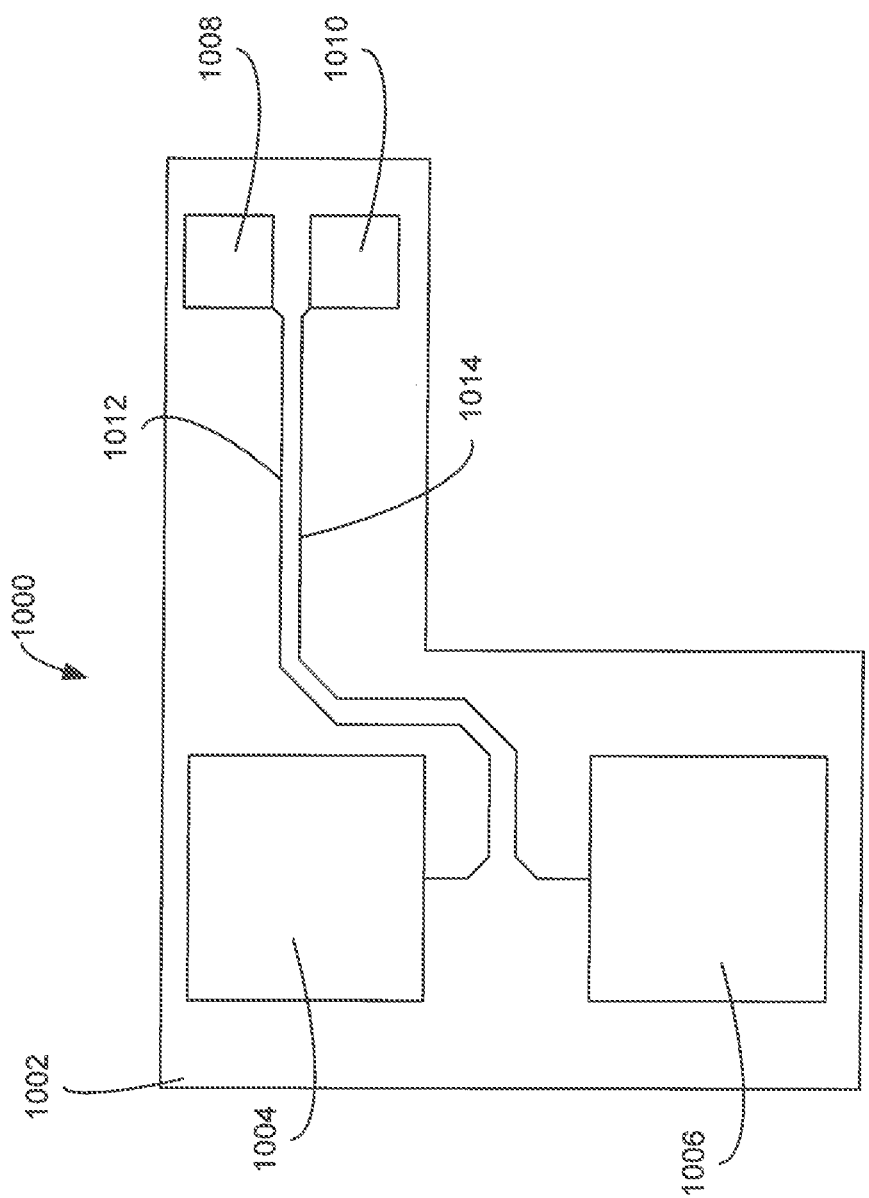
FIG. 10 is a schematic illustration of a PCB assembly including a flexible PCB substrate.

FIG. 10 illustrates an example PCB assembly 1000 in the form of a flexible PCB. The PCB assembly 1000 generally includes a flexible substrate 1002 to which various electronic components may be coupled. As illustrated in FIG. 10, for example, the PCB assembly 1000 includes a pair of electrodes 1004, 1006 coupled to respective contact pads 1008, 1010 by corresponding traces 1012, 1014. Similar to the previously discussed ring-type PCB assemblies, the electrodes 1004, 1006 are merely intended as non-limiting examples of electronic components that may be included in the PCB assembly 1000.

FIGS. 11A and 11B are alternate side elevation views of a distal end 1102 of a tool 1100 including the PCB assembly 1000 of FIG. 10. More specifically, FIG. 11A is a side elevation view of the tool 1100 from a first perspective while FIG. 11B is a side elevation view of the tool 1100 from a perspective 180 degrees offset from the first perspective. Among other things, the tool 1100 may correspond to a catheter, guidewire, or similar elongate tool that may be inserted into a physiological lumen of a patient to perform various functions. As illustrated, the PCB assembly 1000 is disposed on a core 1104 of the tool 1100. During assembly, the PCB assembly 1000 may be disposed on the core 1104 and electrically connected to other components of the tool 1100. For example, the tool 1100 includes a pair of conductors 1106, 1108 that are electrically coupled to the contact pads 1008, 1010 of the PCB assembly 1000 and extend along the length of the core 1104. The conductors 1106, 1108 may in turn be connected to a computing device, power source, or other electrical component at a proximal end of the tool 1100.

As illustrated in FIGS. 11A-11B, the tool 1100 may include an outer sheath 1110 that extends over each of the core 1104 and the PCB assembly 1000. In at least one example implementation of the present disclosure, the tool 1100 may be assembled, in part, by disposing the PCB assembly 1000 onto the core 1104, extending the conductors 1106, 1108 along the core 1104, and electrically coupling the conductors 1106, 1108 to the PCB assembly 1000. Subsequently, the outer sheath 1110 may be extended over the core 1104, the PCB assembly 1000, and the conductors 1106, 1108 and heat shrunk/reflowed to shrink the outer sheath 1110 over the inner components of the tool 1100. In some implementations of the present disclosure, following application of the outer sheath 1110 and similar to FIG. 8F, above, at least a portion of the outer sheath 1110 may be removed (e.g., by cutting or laser ablation) to expose components of the PCB assembly 1000. For example, in FIGS. 11A and 11B the electrodes 1004, 1006 of the PCB assembly 1000 are exposed through the outer sheath 1110. Accordingly, following heat-shrinking/reflowing of the outer sheath 1110, the electrodes 1004, 1006 are free to interact with tissue adjacent the tool 1100 while the other components of the PCB assembly 1000 and the tool 1100 (e.g., the contact pads 1008, 1010, the leads 1012, 1014, and the conductors 1106, 1108) remain substantially covered/protected by the outer sheath 1110.

Figure 12:
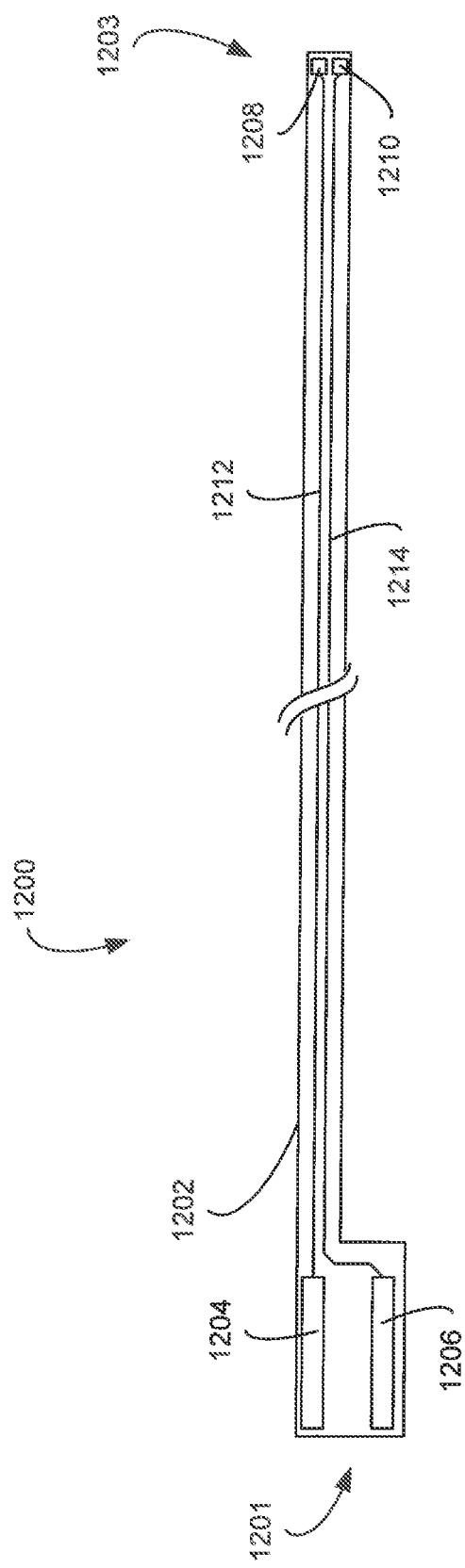
FIG. 12 is a schematic illustration of another flexible PCB assembly in accordance with the present disclosure.

In another aspect of the present disclosure, the general concept of implementing a flexible PCB for electronic components of a tool may be expanded beyond a distally positioned assembly to include additional electrical components of the tool. FIG. 12, for example is a plan view of a PCB assembly 1200 that may be incorporated into a catheter according to the present disclosure. In contrast to the distal tip assembly 1000 of FIG. 10, which is configured to be disposed at a distal end of a catheter, the PCB assembly 1200 is adapted to extend along substantially the full length of a catheter lumen.

As illustrated in FIG. 12, the PCB assembly 1200 includes a PCB substrate 1202 which is formed from a flexible material. In one example implementation, the PCB substrate 1202 may be formed from a polyimide film such as Kapton™.

Although other configurations are possible, the PCB assembly 1200 further includes a pair of electrodes 1204, 1206 disposed at a distal end 1201 of the PCB assembly 1200 and a pair of corresponding contact pads 1208, 1210 disposed at a proximal end 1203 of the PCB assembly 1200. Each of the electrodes 1204, 1206 is electrically coupled to one of the contact pads 1208, 1210 by a respective trace 1212, 1214. Similar to previous implementations discussed herein, the electrodes 1204, 1206 are merely provided as example electronic components and other electronic components (e.g., other electrodes and/or sensors) may be incorporated into the CB assembly 1200 instead of or in addition to the electrodes 1204, 1206. In other implementations, the contact pads 1208, 1210 may instead be replaced by a plug, terminal, or other connector. Alternatively, the traces 1212, 1214 may extend off of the PCB substrate 1202 to facilitate electrical coupling of the traces 1212, 1214 to other components of a tool.

Figure 13A:
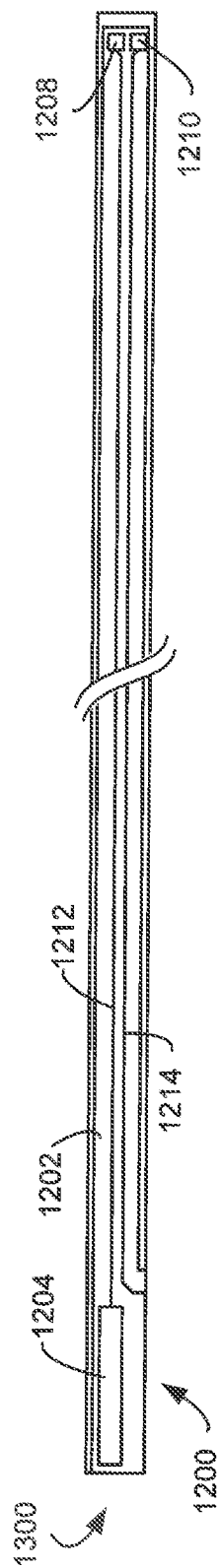
FIGS. 13A and 13B are side views of a tool including the PCB assembly of FIG. 12 without an outer sheath.
Figure 13B:
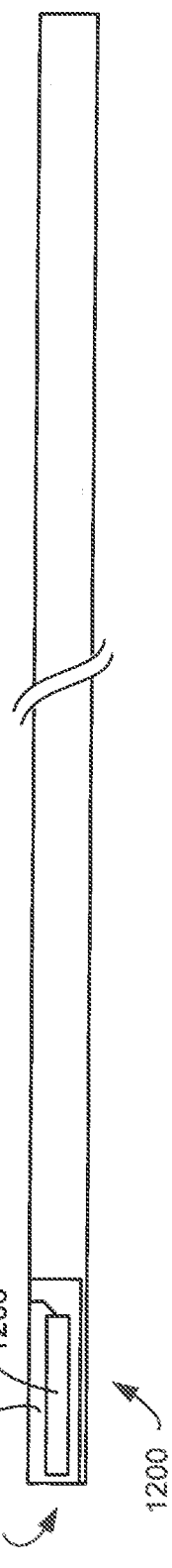
Figure 14A:
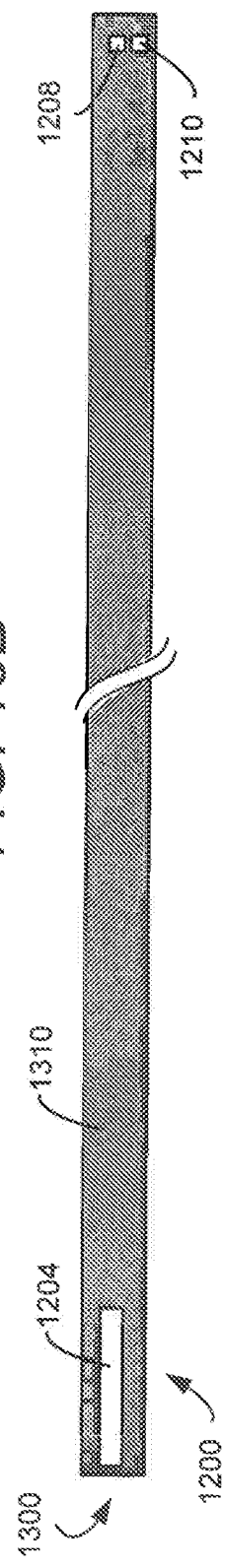
FIGS. 14A and 14B are side views of the tool of FIGS. 13A and 13B including the PCB assembly of FIG. 12 and further including an outer sheath.
Figure 14B:
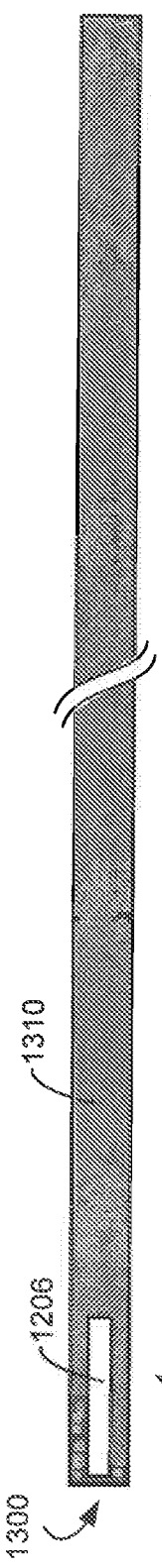

Referring now to FIGS. 13A-14B, an example tool 1300 is illustrated including the PCB assembly 1200 of FIG. 12. More specifically, FIGS. 13A and 14 A are side elevation views of the tool 1300 from a first perspective while FIGS. 13B and 14B illustrate are side elevation views of the tool 1300 from a perspective 180 degrees offset from the first perspective. FIGS. 13A-13B each illustrates the tool 1300 without an outer sheath to more clearly illustrate the arrangement of the PCB assembly 1200 with respect to the remainder of the catheter. In contrast, FIGS. 14A-14B include an outer sheath 1410 that substantially covers the PCB assembly 1200.

Referring to FIGS. 13A-13B, the PCB assembly 1200 is shown extending along a core 1304 of the tool 1300. More specifically, the PCB assembly 1200 is disposed on the core 1304 such that the electrodes 1204, 1206 are disposed at a distal end of the core 1304 and the contact pads 1208, 1210 are disposed at a proximal end of the core 1304. Accordingly, each of the traces 1212, 1214 extends along substantially the full length of the core 1304. As illustrated in FIGS. 13A-14B, in certain implementations the electrodes 1204, 1206 may be spaced relative to each other such that when coupled to the core 1304, the electrode 1204 is disposed opposite the electrode 1206.

The PCB assembly 1200 may be coupled to the core 1304 in various ways. For example, in one implementation, the PCB substrate 1202 of the PCB assembly 1200 may be adhesive backed. In such implementations, assembly of the tool 1300 may include forming or sizing the core 1304 and subsequently laying the PCB assembly 1200 along the core 1304 with the adhesive disposed between the PCB substrate 1202 and the core 1304. Such assembly may further include pressing or otherwise applying pressure to the PCB assembly 1200 to ensure adequate bonding between the PCB substrate 1202 and the core 1304. In certain implementations, the adhesive may be at least partially heat activated such that assembly further includes a step of heating/curing the adhesive after the PCB assembly 1200 has been disposed on the core 1304.

As illustrated in FIGS. 14A and 14B, following coupling of the PCB assembly 1200 to the core 1304, an outer sheath 1310 may be pulled over or otherwise disposed over the core 1304 and the PCB assembly 1200 and cut to size. The outer sheath 1310 may then be heat shrunk/reflowed such that the outer sheath 1310 warp more closely around the core 1304 and the PCB assembly 1200. After wrapping of the outer sheath 1310, portions of the outer sheath 1310 may also be removed (e.g., by cutting, laser ablation, or other suitable method) to expose components of the PCB assembly 1200. For example, as illustrated in FIGS. 14A and 14B, portions of the outer sheath 1310 corresponding to each of the electrodes 1204, 1206 and contact pads 1208, 1210 are removed to expose the electrodes 1204, 1206 and contact pads 1208, 1210.

As previously noted, the PCB assembly 1200 may be adhesive-backed to facilitate coupling of the PCB assembly to the core 1304 of the tool 1300. However, in other implementations, the PCB assembly 1200 may be coupled to the core 1304 in other ways. For example and without limitation, in at least one implementation, the PCB assembly 1200 may not include adhesive backing and may be retained in position by the outer sheath 1310 only. In other implementations, the PCB assembly 1200 may be fixed to the core 1304 using, among other things, ties, clips, wire, or any other suitable coupling mechanism prior to application of the outer sheath 1310.

Figure 15:
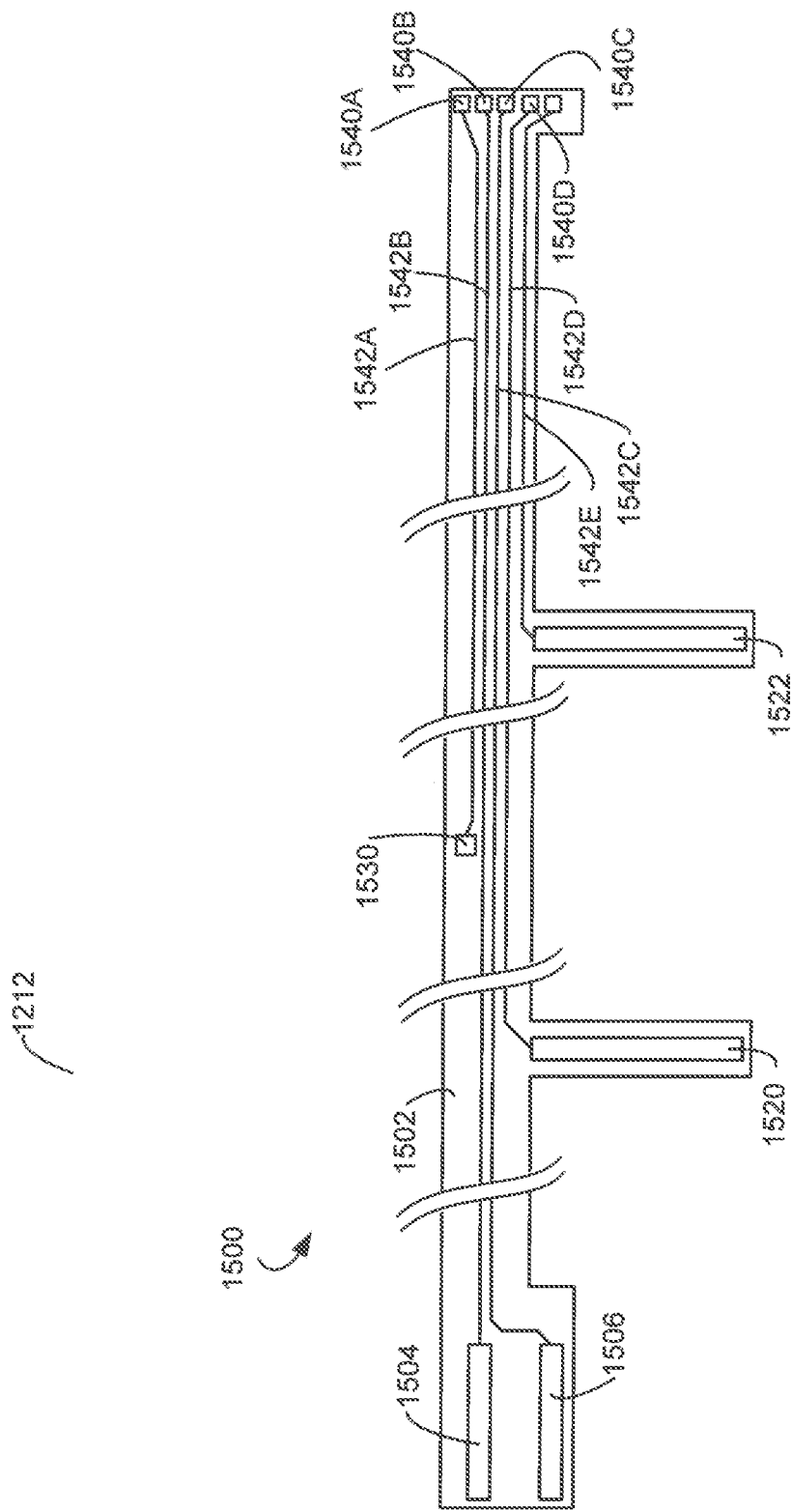
FIG. 15 is a schematic illustration of an alternative PCB assembly according to the present disclosure.

The foregoing examples of distal tip and PCB assemblies generally included electrodes adapted to be disposed at a distal end of a catheter. It should be appreciated, however, that other configurations are contemplated within the scope of the present disclosure. FIG. 15, for example, is a plan view of a PCB assembly 1500 including a flexible PCB substrate 1502 and various electrical components coupled to the PCB substrate 1502. Similar to previous implementations, the PCB substrate 1502 is adapted to be coupled to a core or similar elongate body of a catheter or other tool.

While the PCB assembly 1500 includes a pair of distal electrodes 1504, 1506, the PCB assembly 1500 further includes various other electrical components disposed along its length. For example, the PCB assembly includes each of a first intermediate electrode 1520 and a second intermediate electrode 1522 disposed at respective locations along the PCB substrate 1502. Although other electrode shapes are contemplated, each of the first intermediate electrode 1520 and a second intermediate electrode 1522 are illustrated as extending transversely a primary length 1502 of the PCB substrate 1502. Such an arrangement facilitates wrapping of the intermediate electrodes 1520, 1522 about a core when the PCB assembly 1500 is assembled into a tool. As a result, when fully assembled, the intermediate electrodes 1520, 1522 form ring-like electrodes extending about a core of the tool incorporating the PCB assembly 1500.

The PCB assembly 1500 further includes a sensor 1530 disposed at a location along the PCB substrate 1502. The sensor 1530 is intended to represent any of a wide range of sensors that may be included in the PCB assembly 1500 and that may be used to provide various measurements during use of a catheter including the PCB assembly 1500. For example and without limitation, the sensor 1530 may be any of an accelerometer (e.g., for measuring position, orientation, movement, etc. of the catheter); a pressure, temperature, or flow sensor (e.g., for measuring conditions within a physiological lumen within which the catheter is disposed); or a sensor adapted to measure electrical activity in adjacent tissue. The sensor 1530 may be one of multiple sensors distributed along the PCB substrate 1502.

As illustrated in FIG. 15, each of the electrical components of the PCB assembly 1502 may include one or more respective traces connecting the component to a corresponding contact pad. For example, electrodes 1504, 1506, 1520, and 1522 are illustrated as being electrically coupled to contact pads 1540A-1540D by traces 1542A-1542D and sensor 1530 is illustrated as being electrically coupled to contact pad 1540E by trace 1542E. As previously noted, when assembled into a catheter, the contact pads 1540A-1540E may be electrically coupled to electrical components of a catheter hub including one or more connectors for coupling the catheter to computing devices, monitors, or similar systems. As an alternative to the contact pads 1540A-1540D, the traces 1542A-1542E may be extended off of the PCB substrate 1502, may be replaced by a connector or terminal block, or may otherwise be terminated.

Figure 16:
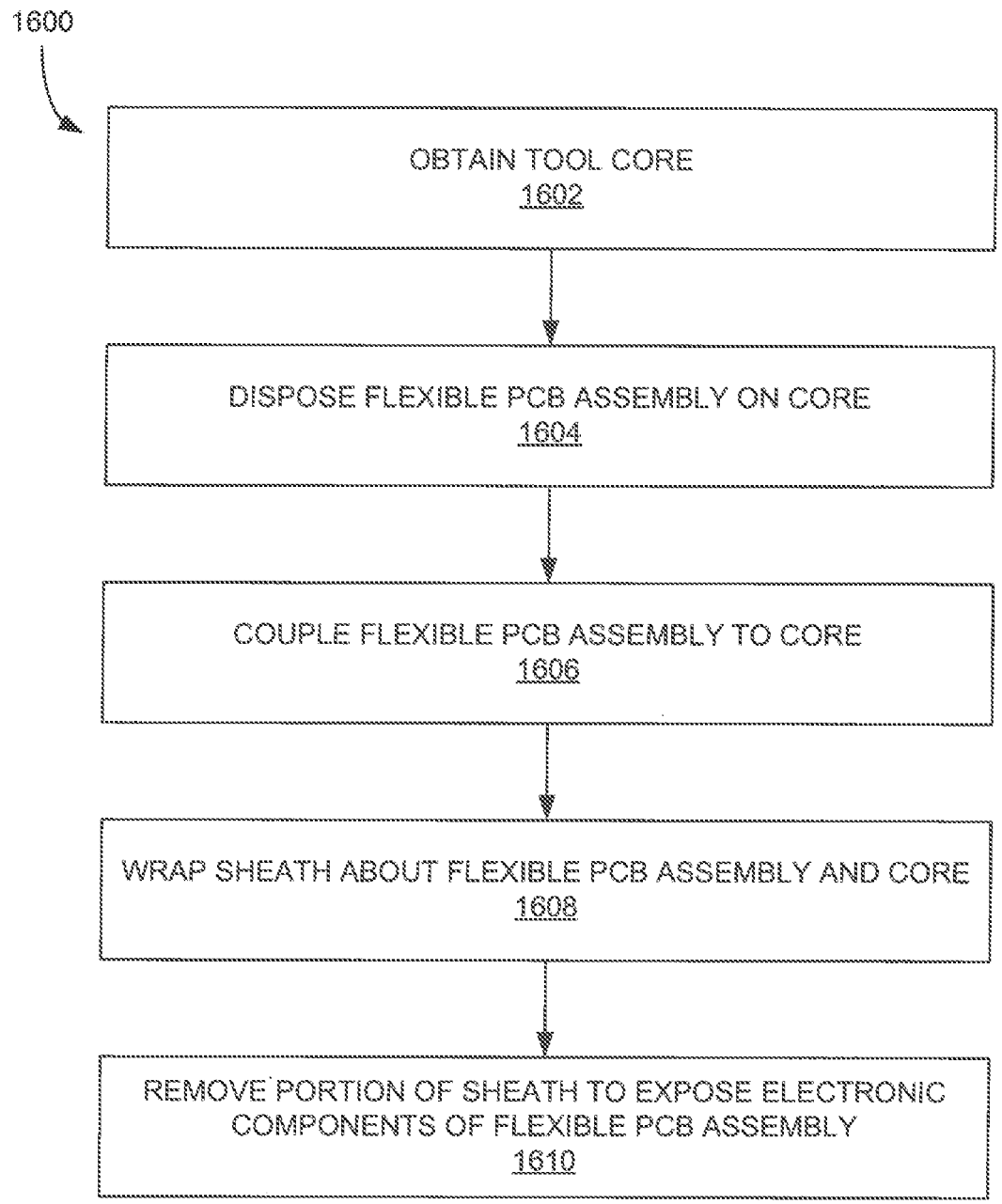
FIG. 16 is a flow chart illustrating another method for assembly a tool in accordance with the present disclosure, the tool including a flexible PCB assembly.

FIG. 16 is a flow chart illustrating a method 1600 of assembly a tool including a flexible PCB assembly, such as the flexible PCB assemblies illustrated in FIGS. 10-15. The method 1600 may be used to manufacture and assembly various types of tools; however, in at least certain implementations, the tool may be a catheter, guide wire, or other elongate tool adapted for insertion into a physiological lumen of a patient.

At operation 1602, a core of the tool is obtained. As previously discussed, the term "core" is used herein to generally refer to an inner structure of the tool. The core may have various constructions. Obtaining the core may include obtaining a prefabricated core or may include at least partially forming the core.

At operation 1604, a flexible PCB assembly is disposed on the core and at operation 1606 the flexible PCB assembly is coupled to the core. In certain implementations, the flexible PCB assembly may include an adhesive-backed PCB substrate such that disposing of the PCB assembly onto the core generally includes laying the PCB substrate on the core, thereby bonding the PCB assembly to the core. Similarly, an adhesive may first be applied to the core followed by disposition of the flexible PCB assembly onto the core. In either case, operations 1604 and 1606 generally overlap in that placing the flexible PCB assembly onto the core and coupling the flexible PCB assembly to the core.

In other implementations, operations 1604 and 1606 may be distinct steps such that the flexible PCB assembly is first disposed onto the core and then coupled to the core. Coupling of the flexible PCB assembly to the core may include applying adhesive, tape, ties, clips, or any other suitable method. Coupling may further include heat-activating or curing an adhesive disposed between the flexible PCB assembly and the core.

In operation 1608, a sheath is wrapped about the flexible PCB assembly and the core. In one example implementation, wrapping of the sheath includes heat-shrinking/reflowing the sheath about the flexible PCB assembly and core. It should be appreciated that wrapping of the sheath about the flexible PCB assembly and the core may also be used to couple the flexible PCB assembly to the core and, as a result, at least a portion of operation 1606 and operation 1606 may occur simultaneously.

In operation 1610, a portion of the sheath is removed to expose electronic components of the flexible PCB assembly, such as electrodes. Removal of the portion of the sheath may be performed by cutting away the portion of the sheath, laser ablating the portion of the sheath, or any other suitable material for removing the portion of the sheath.

Other Applications and Considerations

The previously discussed implementations of the previous disclosure focused primarily on applications involving catheters; however, it should be appreciated that aspects of the present disclosure are more generally applicable to any elongate tool that may be inserted into a physiological lumen of a patient. For example and without limitation, the various PCB assemblies discussed herein may be readily adapted for use with a guide wire where the body of the guide wire forms the core of the tool.

It should also be appreciated that while implementations of the present disclosure primarily focus on electrodes disposed at a distal end of a catheter, the concepts discussed herein may be more generally applied to any electronic components disposed along the length of a catheter or similar elongate tool. Implementations of the present disclosure may more generally include one or more electronic components coupled to a PCB substrate and disposed at any location along an elongate body of a tool. Such electronic components may include, but are not necessarily limited to electrodes, sensors, transmitters, receivers, gauges, switches, transducers, detectors, and antennas.

The foregoing merely illustrates the principles of the present disclosure. Various modifications and alterations to the described illustrative embodiments will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A method of assembling a tool adapted for insertion into a physiological lumen of a patient, the method comprising:
    obtaining a core, the core having an elongate, tubular shape;
    disposing a printed circuit board (PCB) assembly relative to the core so that at least a portion of the PCB assembly is beyond a distal end of the core, the PCB assembly including a PCB substrate and an electronic component disposed on the PCB substrate;
    coupling the PCB substrate to the core;
    electrically coupling the electronic component to a hub coupled to the core; and
    applying an outer sheath about the core and the PCB assembly so that a first portion of the outer sheath surrounds and extends along a distal segment of the core at the distal end and a second portion of the outer sheath surrounds and extends along the PCB substrate.

2. The method of claim 1, wherein the PCB substrate includes an adhesive backing and is contact with the distal segment of the core, wherein coupling the PCB substrate to the core comprises bonding the PCB substrate to the core using the adhesive backing.

3. The method of claim 1, wherein coupling the PCB substrate to the core comprises shrinking the outer sheath while the outer sheath surrounds the core and the PCB substrate so that the outer sheath forms a joint between the core and the PCB substrate.

4. The method of claim 1, further comprising, after applying the outer sheath, removing a portion of the outer sheath to expose the electronic component.

5. The method of claim 1, wherein the PCB substrate is preformed into a rigid or semi-rigid ring shape.

6. The method of claim 1, further comprising forming the PCB substrate into a ring shape.

7. The method of claim 1, wherein PCB substrate is flexible and coupling the PCB substrate to the core comprises wrapping the PCB substrate about the distal segment of the core.

8. The method of claim 1, wherein the PCB assembly includes a terminal point and a trace extending along the PCB substrate, and wherein electrically coupling the electronic component to the hub includes electrically coupling the terminal point to the hub.

9. The method of claim 8, wherein
    the PCB substrate extends distally from a proximal end of the core, the terminal point is disposed at the proximal end of the core, and
    the electronic component is disposed distally from the terminal point.

10. The method of claim 1, wherein the electronic component is an electrode.

11. The method of claim 1, wherein the electronic component is an electrode that extends circumferentially about the core.

12. The method of claim 1, wherein the PCB substrate is a rigid or semi-rigid preformed ring that includes a split, and the PCB substrate is configured to deflect to enable the core to be loaded into a lumen of the preformed ring through the split.

13. The method of claim 1, wherein the core is a catheter shaft.

14. The method of claim 1, wherein the electronic component is a sensor.

15. The method of claim 1, wherein disposing the PCB assembly relative to the core comprises positioning a pull ring axially located, along a length of the tool, between the core and the PCB assembly.

16. The method of claim 15, wherein applying the outer sheath about the core and the PCB assembly comprises applying the outer sheath about the pull ring so that a third portion of the outer sheath surrounds and extends along the pull ring, the third portion disposed between the first portion and the second portion.

17. A method of assembling a tool adapted for insertion into a physiological lumen of a patient, the method comprising:
    obtaining a core, the core having an elongate, tubular shape;
    disposing a printed circuit board (PCB) assembly relative to the core so that at least a portion of the PCB assembly is beyond a distal end of the core, the PCB assembly including a PCB substrate, a first electrode disposed on the PCB substrate and electrically coupled to a first terminal point of the PCB assembly, and a second electrode disposed on the PCB substrate and electrically coupled to a second terminal point of the PCB assembly;

coupling the PCB substrate to the core;

electrically coupling each of the first terminal point and the second terminal point to a hub coupled to the core; and applying an outer sheath about the core and the PCB assembly so that a first portion of the outer sheath surrounds and extends along a distal segment of the core at the distal end and a second portion of the outer sheath surrounds and extends along the PCB substrate.

18. The method of claim 17, wherein, after applying the outer sheath, each of the first electrode and the second electrode is exposed through the outer sheath.

19. A method of assembling a tool adapted for insertion into a physiological lumen of a patient, the method comprising:

obtaining a core, the core having an elongate, tubular shape;

mounting a printed circuit board (PCB) assembly onto a distal segment of the core, the PCB assembly including a PCB substrate and an electronic component disposed on the PCB substrate, the PCB substrate having a rigid or semi-rigid preformed ring shape and including a split, wherein the PCB assembly is mounted to the core by pressing the core through the split in the PCB substrate;

electrically coupling the electronic component to a hub coupled to the core; and applying an outer sheath about the core and the PCB assembly so that the outer sheath surrounds and extends along both the distal segment of the core and the PCB substrate.

20. The method of claim 19, wherein the PCB assembly is mounted onto the distal segment of the core so that the PCB assembly projects beyond a distal end of the core, and wherein the outer sheath is applied about the core and the PCB assembly so that a first portion of the outer sheath surrounds and extends along the distal segment of the core and a second portion of the outer sheath surrounds and extends along the PCB substrate without surrounding and extending along the core.

* * * * *